United States Patent [19]

Hashiba et al.

[11] Patent Number: 4,537,984

[45] Date of Patent: Aug. 27, 1985

[54] PROCESS FOR PRODUCING 2-(4-HYDROXYPHENOXY) PROPIONATE DERIVATIVES

[75] Inventors: Isao Hashiba; Tadashi Nishikimi; Shuji Tsuchiya, all of Funabashi, Japan

[73] Assignee: Nissan Chemical Industries Ltd., Tokyo, Japan

[21] Appl. No.: 604,156

[22] Filed: Apr. 26, 1984

[30] Foreign Application Priority Data

May 19, 1983 [JP] Japan .................................. 58-88097
Oct. 8, 1983 [JP] Japan .................................. 58-188889

[51] Int. Cl.$^3$ ............................................. C07C 69/76
[52] U.S. Cl. ..................................... 560/061; 560/53; 562/471
[58] Field of Search ......................... 560/61; 562/471

[56] References Cited

FOREIGN PATENT DOCUMENTS

| 0082413 | 8/1982 | European Pat. Off. ............ 560/061 |
| 2003430 | 8/1969 | Fed. Rep. of Germany ...... 560/061 |
| 5079344 | 6/1980 | Japan ................................... 560/061 |
| 8100101 | 8/1981 | PCT Int'l Appl. ................. 560/061 |

*Primary Examiner*—Paul J. Killos
*Attorney, Agent, or Firm*—Oblon, Fisher, Spivak, McClelland & Maier

[57] ABSTRACT

A process for producing a 2-(4-hydroxyphenoxy) propionate derivative represented by the formula:

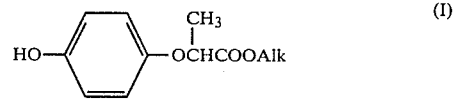

(I)

where Alk is a $C_1$-$C_5$ alkyl group, which comprises reacting a phenoxy propionate derivative represented by the formula:

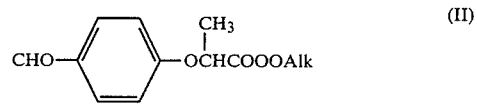

(II)

where Alk is as defined above, with a peroxide to obtain a formate derivative represented by the formula:

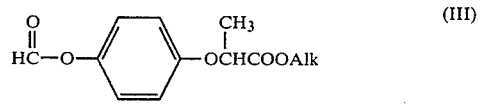

(III)

where Alk is as defined above, and hydrolyzing the formate of the formula III.

2 Claims, No Drawings

PROCESS FOR PRODUCING 2-(4-HYDROXYPHENOXY) PROPIONATE DERIVATIVES

The present invention relates to a process for producing a 2-(4-hydroxyphenoxy)propionate derivatives represented by the general formula:

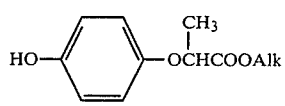
(I)

where Alk is a $C_1$–$C_5$ alkyl group.

2-(4-Hydroxyphenoxy)propionates are useful as intermediates for the compounds disclosed in German Unexamined Patent Publications No. 2812571, No. 2640730 and No. 3004770.

As a process for the production of such 2-(4-hydroxyphenoxy)propionate derivatives, Japanese Unexamined Patent Publication No. 59718/1981 discloses a process shown by the following formula:

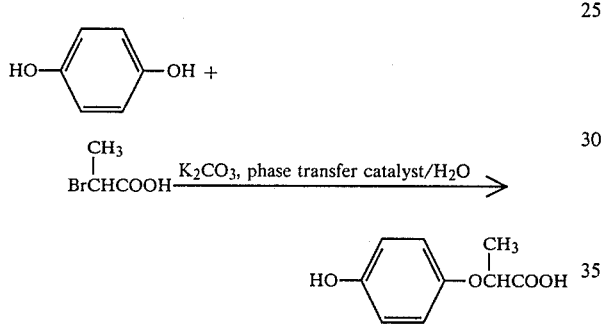

Further, International application Publication No. 82/639 discloses a process shown by the following formula:

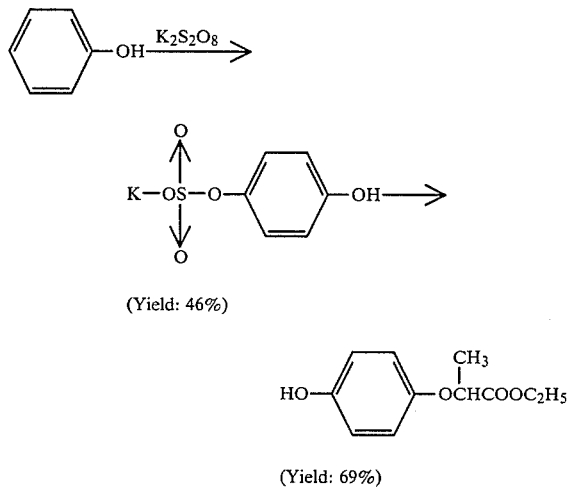

(Yield: 69%)

However, the process disclosed in Japanese Unexamined Patent Publication No. 59718/1981 has drawbacks such that a considerable amount of a disubstituted compound is produced as by-product, and unreacted hydroquinone remains. Accordingly it is impossible to obtain 2-(4-hydroxyphenoxy)propionic acid in good yield and with high purity. According to this process, the propionic acid is obtainable. In order to obtain the desired ester, it is further required to esterify the acid thus obtained, such being not industrially advantageous.

Whereas, the process disclosed in International application Publication No. 82/639, is not industrially advantageous because the yield in the step for synthesizing the sulfate is low.

The present inventors have found that the desired 2-(4-hydroxyphenoxy)propionate can be obtained in good yield under a mold condition in a simple process with no substantial formation of by-products by using, as starting material, p-hydroxy benzaldehyde which is industrially readily available. The present invention has been accomplished based on this discovery.

Namely, the present invention provides a process for producing a 2-(4-hydroxyphenoxy)propionate derivative represented by the formula:

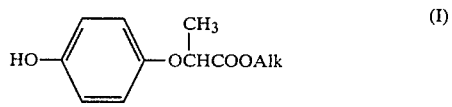
(I)

where Alk is a $C_1$–$C_5$ alkyl group, which comprises reacting a phenoxy propionate derivative represented by the formula:

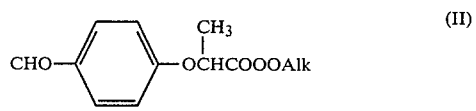
(II)

where Alk is as defined above, with a peroxide to obtain a formate derivative represented by the formula:

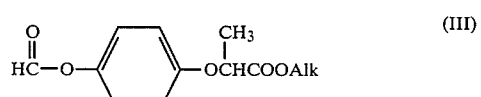
(III)

where Alk is as defined above, and hydrolyzing the formate of the formula III.

The phenoxy propionate derivative of the formula II may be prepared in accordance with the following Scheme.

Scheme 1

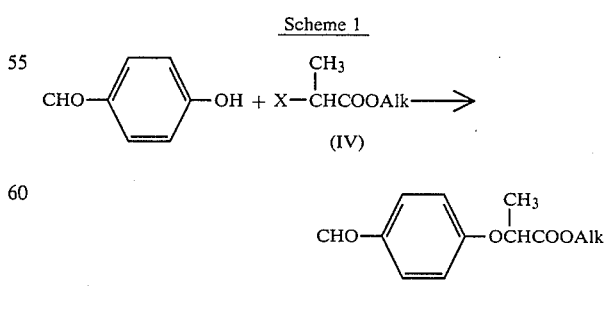

where Alk is a $C_1$–$C_5$ alkyl group, and X is a halogen atom or a

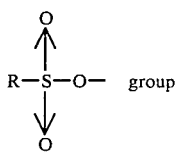

(where R is a lower alkyl group, a phenyl group or a substituted phenyl group).

Namely, p-hydroxybenzaldehyde is condensed with an α-substituted propionate derivative of the formula IV in an organic solvent in the presence of a base, whereby a phenoxy propionate derivative of the formula II can be prepared.

As the base, there may be employed carbonates such as sodium carbonate, potassium carbonate, sodium hydrogen carbonate and potassium hydrogen carbonate. They may be used alone or in combination as a mixture. The amount of the base is usually from 1.0 to 10 times, preferably from 1.2 to 2.0 times in equivalent, relative to 4-hydroxybenzaldehyde. As the solvent, a polar solvent is usually employed such as dimethylformaide, dimethylsulfoxide, N,N-dimethylimidazolidinone or N-methylpyrrolidone. However, an aromatic hydrocarbon solvent such as benzene or toluene may be used in combination with from 99 to 10% by weight of the above-mentioned polar solvent. The amount of the solvent is usually from 2 to 10 times the weight of the 4-hydroxybenzaldehyde. The reaction temperature may be from 50° to 150° C. However, it should preferably be from 50° to 100° C., since hydrolysis is likely to take place at a high temperature. Further, the reaction may sometimes be slow depending upon the reaction conditions. In such a case, the reaction may be facilitated by adding a phase transfer catalyst such as trimethylbenzylammonium chloride in an amount of from 0.01 to 0.1 time the weight of the 4-hydroxybenzaldehyde. Potassium iodide has a similar effect.

In order to isolate the phenoxy propionate derivative of the formula II, in the case where the conversion is high, the reaction mixture is filtered to separate off the inorganic salt and then subjected to distillation under reduced pressure, or in the case where unreacted materials remain to some extent, a water-insoluble solvent such as toluene and water are added to remove the inorganic salt, then the organic solvent layer is washed with a proper amount of a 1 to 2% sodium hydroxide aqueous solution, and after distilling off the solvent, subjected to a distillation under reduced pressure.

The α-substitued propionate derivative of the formula IV has an optical isomer of the formula IV' attributable to the asymmetric carbon at α-position to the carboxyl group. In the reaction of Scheme 2 below, this optical isomer of the formula IV' does not undergo racemization which usually takes place by the condensation reaction under the above-mentioned alkaline conditions, but gives an optically active desired product of the formula II' in high optical purity.

Scheme 2

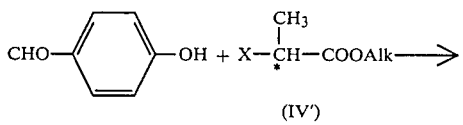

(IV')

-continued
Scheme 2

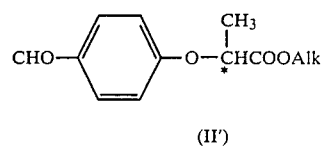

(II')

where Alk and X are as defined above.

In order to obtain a desired 2-(4-hydroxyphenoxy)-propionate derivative of the formula I, the phenoxy propionate derivative of the formula II thus obtained is subjected to an oxidation reaction known as Baeyer-Villiger reaction to obtain the formate derivative of the formula III, which is then hydrolized.

Scheme 3

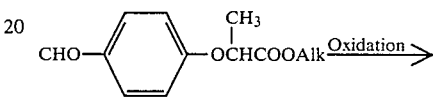

(II)

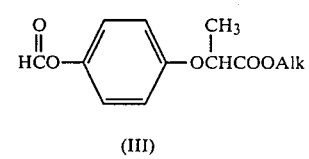

(III)

where Alk is as defined above.

Scheme 4

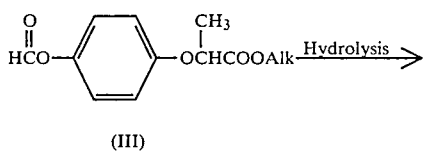

(III)

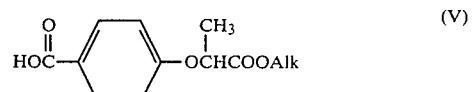

(I)

where Alk is as defined above.

The formate derivative of the formula III may or may not be isolated before being subjected to the subsequent hydrolysis to obtain a 2-(4-hydroxyphenoxy)propionate derivative of the formula I.

In the reaction of Scheme 3 which is commonly known as Baeyer-Villiger reaction, it is possible that a benzoic acid derivative represented by the formula:

$$\underset{HOC}{\overset{O}{\parallel}}\text{—}\underset{}{\bigcirc}\text{—OCHCOOAlk} \qquad (V)$$
$$\phantom{HOC—\bigcirc—O}\overset{CH_3}{\underset{|}{}}$$

where Alk is a $C_1$–$C_5$ alkyl group, forms in addition to the formate derivative of the formula III. Organic Reaction Vol 9, 73p, John Wiley & Sons Inc. presents a detailed review on Baeyer-Villiger reaction. According to the review, in the case of 4-methoxybenzaldehyde which is structurally similar to the starting material of the present invention, 4-methoxybenzoic acid corresponding to the compound of the formula V is produced quantitatively. Whereas, in the process of the present invention, contrary to such an expectation, no formation of the compound of the formula V was observed, and only the formate derivative of the formula III or its hydrolyzate i.e. 2-(4-hydroxyphenoxy)propionate derivative is obtained.

As an oxidating agent to be used for the reaction of Scheme 3, there may be mentioned an organic peroxide such as peracetic acid, perbenzoic acid, m-chloroperbenzoic acid or benzoyl peroxide. A combination of hydrogen peroxide and a catalytically effective amount of peracetic acid may also be employed. Such an oxidizing agent is usually employed in an amount of from 1.0 to 2.0 mols, preferably from 1.1 to 1.4 mols. The excess amount of the peroxide may be decomposed by Fe ions or washed away with an aqueous solution of a reducing agent such as sodium sulfite or sodium hydrogen sulfite. The reaction may be conducted in the absence of a solvent. However, an inert solvent may be used as the case requires. As such a solvent, there may be employed an organic hydrocarbon solvent such as benzene or toluene, or a halogen-type solvent such as methylene chloride. The reaction temperature is usually from 0° to 70° C., preferably from 20° to 50° C. For the hydrolysis of the resulting formate, a temperature condition similar to the case of the oxidation may be employed. Water is used in an amount of from 1 to 20 molar times. The hydrolysis is usually conducted in the same reaction vessel. However, the hydrolysis may be conducted after the separation, under a similar condition by using a catalytically effective amount of a mineral acid or an organic acid. After the completion of the reaction, the reaction mixture is washed with water, if necessary, after the addition of a solvent for extraction such as toluene, followed by washing with an aqueous sodium hydrogen carbonate solution, then with an aqueous sodium hydrogen sulfite solution, and further with water. Then, the solvent was distilled off and the residue is distilled under reduced pressure to obtain a 2-(4-hydroxyphenoxy)propionate.

The optical purity of a 2-(4-hydroxyphenoxy)propionate obtainable from an optically active 2-(4-formylphenoxy)propionate by the oxidation and hydrolysis under the above-mentioned reaction conditions, is substantially the same as that of the starting material.

Now, the present invention will be described in further detail with reference to Examples and Reference Examples. However, it should be understood that the present invention is by no means restricted by these Examples. In the following Examples and Reference Examples, the optical rotation was measured with respect to a 3% chloroform solution, and the optical purity was measured by NMR with use of a shift reagent and the enantiomer excess (e.e.) value was obtained.

REFERENCE EXAMPLE 1

6.1 g of 4-hydroxybenzaldehyde, 7 g of ethyl α-chloropropionate, 4 g of sodium carbonate, 0.2 g of potassium iodide and 20 g of dimethyl formamide, were mixed, and the mixture was stirred at 100° C. for 5 hours and then cooled to room temperature. The inorganic salts were filtered off, and the residue was washed with dimethylformamide. The solution from the washing was combined with the filtrate, followed by concentration and distillation under reduced pressure, whereby 10.3 g of ethyl 2-(4-formylphenoxy)propionate was obtained as a colorless transparent liquid. The boiling point was from 130° to 140° C./1 mmHg.

REFERENCE EXAMPLE 2

6.1 g of 4-hydroxybenzaldehyde, 9 g of n-butyl α-chloropropionate, 4 g of sodium carbonate, 0.2 g of potassium iodide and 20 g of dimethyl formamide, were mixed, and the mixture was stirred at 100° C. for 5 hours and then cooled to room temperature. The inorganic salts were filtered off and washed with dimethylformamide. The solution from the washing was combined with the filtrate, followed by concentration and distillation under reduced pressure, whereby 11.3 g of butyl 2-(4-formylphenoxy)propionate was obtained as a colorless transparent liquid. The boiling point was from 135 to 140° C./0.1 mmHg.

REFERENCE EXAMPLE 3

6.1 g of 4-hydroxybenzaldehyde, 10.8 g of (−)-ethyl lactate-mesylate ($[\alpha]_D^{25} = -54°$, optical purity: 96%), 4 g of potassium carbonate, 0.2 g of potassium iodide and 100 g of dimethyl formamide, were mixed, and the reaction was stirred at 100° C. for 5 hours and then cooled to room temperature. The reaction mixture was subjected to liquid separation with an addition of toluene and water. The organic layer was washed twice with water, and after distilling off toluene, subjected to distillation under reduced pressure, whereby 8.9 g of (+)-ethyl 2-(4-formylphenoxy)propionate was obtained as a colorless transparent liquid. The boiling point was from 130° to 140° C./1 mmHg.
$[\alpha]_D^{25} = +51.3°$, optical purity; 93%

REFERENCE EXAMPLE 4

6.1 g of 4-hydroxybenzaldehyde, 12.3 g of (−)-butyl lactate-mesylate ($[\alpha]_D^{25} = -49.1°$), 4 g of sodium carbonate, 0.2 g of potassium iodide and 100 g of dimethyl formamide, were mixed, and the mixture was stirred at 100° C. for 5 hours and then cooled to room temperature. The reaction mixture was subjected to liquid separation with an addition of toluene and water. The organic layer was washed twice with water, and after distilling off toluene, subjected to distillation under reduced pressure, whereby 10.3 g of (+)-butyl 2-(4-formylphenoxy)propionate was obtained as a colorless transparent liquid. The boiling point was from 135° to 140° C./0.1 mmHg.
$[\alpha]_D^{25} = +44.1°$

REFERENCE EXAMPLE 5

12.2 g of 4-hydroxybenzaldehyde, 30 g of (−)-ethyl lactate-tosylate ($[\alpha]_D^{25} = -34.2°$, optical purity: 96%), 20 g of potassium carbonate and 100 g of acetonitrile, were mixed, and the mixture was refluxed for 5 hours and then cooled to room temperature. The reaction mixture was treated in the same manner as in Reference Example 3, whereby 20.0 g of (+)-ethyl 2-(4-hydroxyphenoxy)propionate was obtained as a colorless transparent liquid. The boiling point was from 130° to 140° C./1 mmHg. $[\alpha]_D^{25} = +51.5°$, optical purity: 93%.

REFERENCE EXAMPLE 6

20.0 g of hydroquinone monobenzyl ether, 21.6 g of (−)-ethyl lactate-mesylate ($[\alpha]_D^{25} = -54.0°$, optical purity: 96%), 20 g of potassium carbonate, 0.5 g of potassium iodide and 100 g of dimethyl formamide, were mixed, and the mixture was reacted at from 80° to 100° C. for 5 hours and then cooled to room temperature. The reaction mixture was subjected to liquid separation with an addition of toluene and water. The organic layer was washed twice with water, and after distilling off toluene, subjected to distillation under reduced pressure, whereby 26.5 of (+)-ethyl 2-(4-benzyloxyphenoxy)propionate was obtained as a colorless transparent liquid. The boiling point was 180° C./0.5 mmHg.

$[\alpha]_D^{25} = +6.4°$, optical purity: 18%.

To 5 g of (+)-ethyl 2-(4-benzyloxyphenoxy)propionate thus obtained, 20 g of ethanol and 1 g of 5% Pd-C were added, and then hydrogen was reacted therewith under atmospheric pressure at 25° to 30° C. The catalyst was filtered off, and ethanol was distilled off. The residue was subjected to distillation under reduced pressure, whereby 3 g of (+)-ethyl 2-(4-hydroxyphenoxy)propionate was obtained.

$[\alpha]_D^{25} = +8.0°$, optical purity: 18%

EXAMPLE 1

While stirring a mixture of 22.2 g of ethyl 2-(4-formylphenoxy)propionate and 60 g of toluene at room temperature, 22.8 g of 40% peracetic acid was dropwise added. After stirring at 20° to 30° C. for 2 hours and at 50° C. for 2 hours, 2.0 g of water was added and the mixture was stirred for 2 hours. The reaction mixture was cooled to room temperature, and 40 g of water was added. The aqueous layer was separated. The organic layer was washed with 40 g of water, followed by washing twice with 40 g of a 5% sodium hydrogen carbonate aqueous solution, further with 40 g of a 5% sodium hydrogen sulfite aqueous solution and then with 40 g of water. Then, the organic layer was concentrated by distilling off toluene under reduced pressure, and then subjected to distillation under reduced pressure, whereby 16.5 g of ethyl 2-(4-hydroxyphenoy)propionate was obtained as a colorless transparent liquid. The boiling point was from 130° to 140° C./1 mmHg.

EXAMPLE 2

While stirring a mixture of 25 g of butyl 2-(4-formylphenoxy)propionate and 75 g of toluene at room temperature, 22.8 g of 40% peracetic acid was dropwise added. After stirring at 20° to 30° C. for 2 hours and at 50° C. for 2 hours, 2.0 g of water was added, and the mixture was stirred for 2 hours. The reaction mixture was cooled to room temperature and subjected to the same after-treatment as in Example 1, whereby 19.5 g of butyl 2-(4-hydroxyphenoxy)propionate was obtained as a colorless transparent liquid by the distillation under reduced pressure. The boiling point was 160° C./1 mmHg.

EXAMPLE 3

A mixture of 2.2 g of ethyl 2-(4-formylphenoxy)propionate, 10 ml of methylene chloride and 2.6 g of m-chloroperbenzoic acid, were reacted for 2 hours under reflux, and after an addition of 0.5 g of water, further refluxed for 1 hour. After cooling, the reaction mixture was washed twice with 20 g of a 5% sodium hydrogen carbonate aqueous solution, then with 10 g of 5% sodium hydrogen sulfite aqueous solution and further with 10 g of water. The mixture was concentrated by distilling off methylene chloride, and then subjected to distillation under reduced pressure, whereby 1.1 g of ethyl 2-(4-hydroxyphenoxy)propionate was obtained as a colorless transparent liquid. The boiling point was from 130° to 140° C./1 mmHg.

EXAMPLE 4

While stirring a mixture of 22.5 g of ethyl 2-(4-formylphenoxy)propionate ($[\alpha]_D^{25} = +51.5°$) and 60 g of toluene at room temperature, 22.8 g of 40% peracetic acid was dropwise added. After stirring at 20° to 30° C. for 2 hours and at 50° C. for 2 hours, 0.2 g of water was added, and the mixture was stirred for 2 hours. After cooling the reaction mixture to room temperature, 40 g of water was added. The aqueous layer was separated. The organic layer was washed with 40 g of water, followed by washing twice with 40 g of a 5% sodium hydrogen carbonate aqueous solution, then with 40 g of a 5% sodium hydrogen sulfite aqueous solution and further with 40 g of water. Then, the reaction mixture was concentrated by distilling off toluene under reduced pressure, and subjected to distillation under reduced pressure, whereby 16.5 g of (+)-ethyl 2-(4-hydroxyphenoxy)propionate was obtained as a colorless transparent liquid. The boiling point was from 130° to 140° C./1 mmHg.

$[\alpha]_D^{25} = +42.0°$, optical purity: 93%

EXAMPLE 5

While stirring a mixture of 25 g of (+)-butyl 2-(4-formylphenoxy)propionate ($[\alpha]_D^{25} = +44.1°$) and 75 g of toluene at room temperature, 22.8 g of 40% peracetic acid was dropwise added. After the reaction at 50° C. for 2 hours, the reaction mixture was subjected to liquid separation with an addition of water. The toluene layer was separated and washed with water. To the toluene layer, 25 g of sodium hydrogen carbonate and water was added, and the mixture was reacted at 50° C. for 5 hours. Then, the reaction mixture was subjected to liquid separation. The organic layer was washed twice with water. The organic layer was concentrated by distilling off toluene, and then subjected to distillation under reduced pressure, whereby 19.0 g of (+)-butyl 2-(4-hydroxyphenoxy)propionate was obtained as a colorless transparent liquid. The boiling point was 160° C./1 mmHg.

$[\alpha]_D^{25} = +36.7°$

EXAMPLE 6

A mixture of 2.2 g of (+)-ethyl 2-(4-formylphenoxy)propionate ($[\alpha]_D^{25} = +51.3°$ optical purity: 93%), 10 ml of methylene chloride and 2.6 g of m-chloroperbenzoic acid, was reacted for 2 hours under reflux, and after an addition of 0.5 g of water, further refluxed for 1 hour. After cooling, the reaction mixture was washed twice with 20 g of a 5% sodium hydrogen carbonate aqueous solution, then with 10 g of a 5% sodium hydrogen sulfite aqueous solution and further with 10 g of water. Then, the reaction mixture was concentrated by distilling off methylene chloride and then subjected to distillation under reduced pressure, whereby 1.1 g of ethyl 2-(4-hydroxyphenoxy)propionate was obtained as a colorless transparent liquid. The boiling point was from 130° to 140° C./1 mmHg. $[\alpha]_D^{25} = +40.6°$, optical punity: 90%

We claim:

1. A process for producing a 2-(4-hydroxyphenoxy)propionate derivative represented by the formula:

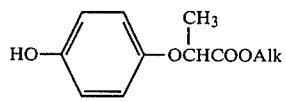  (I)

where Alk is a $C_1$–$C_5$ alkyl group, which comprises reacting a phenoxy propionate derivative represented by the formula:

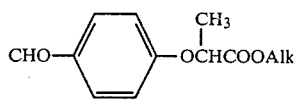  (II)

where Alk is as defined above, with a peroxide to obtain a formate derivative represented by the formula:

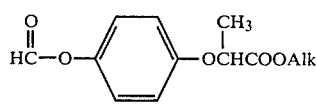  (III)

where Alk is as defined above, and hydrolyzing the formate of the formula III.

2. The process according to claim 1, wherein the optical isomer of a p-hydroxy phenoxy propionate derivative represented by the formula:

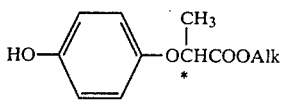  (I′)

where Alk is a $C_1$–$C_5$ alkyl group, is prepared by reacting an optical isomer of a phenoxy propionate derivative represented by the formula:

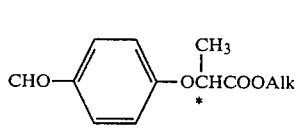  (II′)

where Alk is as defined above, with a peroxide to obtain a formate derivative represented by the formula:

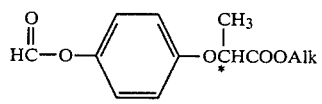  (III′)

where Alk is as defined above, and hydrolyzing the formate of the formula III′.

* * * * *